United States Patent [19]

Eliash et al.

[11] Patent Number: 5,298,131
[45] Date of Patent: Mar. 29, 1994

[54] METHOD OF MONITORING METAL ION CONTENT IN PLATING BATHS

[75] Inventors: Bruce M. Eliash, Los Angeles; Frank A. Ludwig, Rancho Palos Verdes; Nguyet H. Phan, Los Angeles, all of Calif.; Vilambi N. Reddy, Jamaica, N.Y.

[73] Assignee: Hughes Aircraft Company, Los Angeles, Calif.

[21] Appl. No.: 68,030

[22] Filed: May 28, 1993

[51] Int. Cl.$^5$ .............................................. G01N 27/26
[52] U.S. Cl. .................. 204/153.1; 204/412; 204/434; 204/DIG. 8
[58] Field of Search .................. 204/412, 434, 153.1, 204/405, DIG. 8, DIG. 9; 205/81, 101–105

[56] References Cited

U.S. PATENT DOCUMENTS 4,631,116 12/1986 Ludwig ............................... 204/434

OTHER PUBLICATIONS

EG&G Princeton Applied Research, Application Note Plat-2, "Application of Polargraphy to the Plating Industry," 1985.*

Primary Examiner—John Niebling
Assistant Examiner—Bruce F. Bell
Attorney, Agent, or Firm—M. E. Lachman; M. W. Sales; W. K. Denson-Low

[57] ABSTRACT

A method of monitoring in-tank and on-line metal ion content within a plating bath. The method involves the steps of applying a pretreatment signal to a sensing electrode positioned within the plating bath, applying a sweep signal to the pretreated sensing electrode, and measuring the voltammetric peak current of the resultant response signal. The voltammetric peak current is proportional to the metal ion content of the plating bath. The method complements and is easily integrated with known voltammetric techniques for analysis of trace and major constituents, and is thus an integral part of an efficient overall plating bath analysis system.

16 Claims, 2 Drawing Sheets

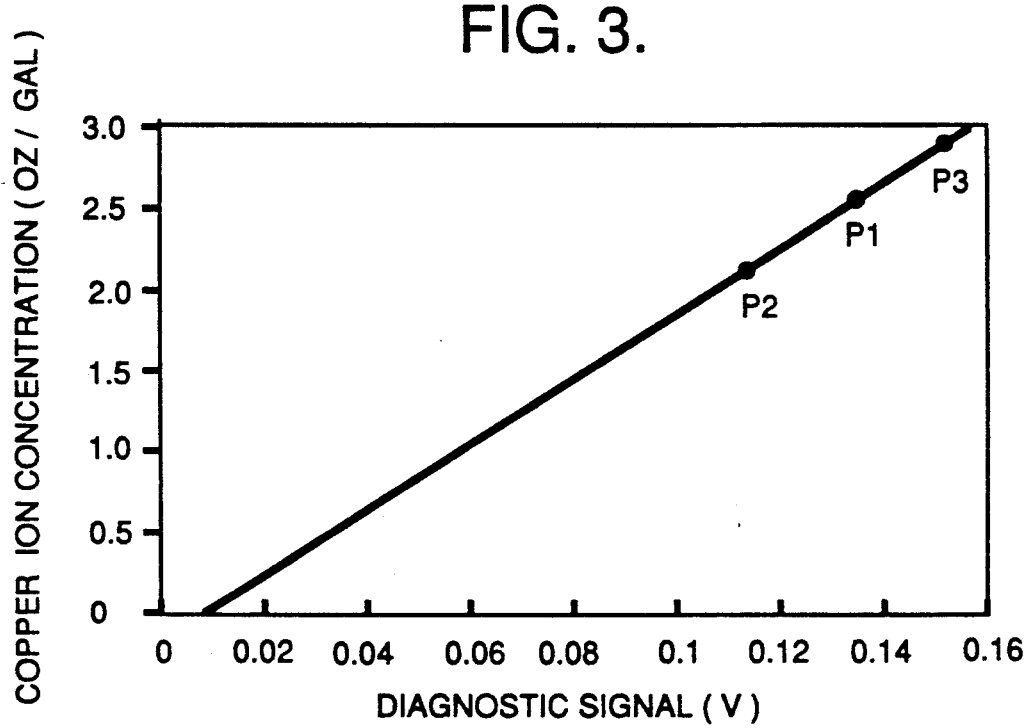

METHOD OF MONITORING METAL ION CONTENT IN PLATING BATHS

BACKGROUND OF THE INVENTION

Field of the Invention

The present invention relates generally to plating baths and methods for monitoring the constituents contained therein. More particularly, the method of the present invention relates to a voltammetric analysis method which accurately indicates metal ion concentrations within the bath. The method can be used to maintain desired metal ion concentrations in order to ensure optimal plating bath performance.

Description of Related Art

A typical plating bath solution is comprised of a combination of several distinct electrochemical constituents which can be broadly divided into major constituents and trace constituents. The major constituents typically make up about 2 to 30 percent of the total bath weight or volume. Trace constituents are present in smaller quantities, usually less than 1 percent of the total weight or volume. Metal ions are the source of plated metal, and, therefore, are an important type of major constituent found in all plating baths.

The concentration levels of both major and trace constituents will influence the quality of the resultant plating deposit, and should therefore be regularly monitored. Methods have been developed for in-tank monitoring of trace constituents as well as certain major constituents. For example, U.S. Pat. No. 4,631,116 discloses a method for monitoring trace constituents such as organic addition agents using an in-tank electrochemical sensor. The above patent is owned by the same assignee as the present invention and is hereby incorporated by reference.

In general, the high concentrations of metal ions in their respective plating baths can interfere with voltammetric analysis and other wet chemical measurement techniques. Therefore, a sample of the plating bath solution is usually drawn from the plating tank and diluted or added to a buffer solution prior to analysis of metal ion concentration. Supporting electrolytes may then be added to the diluted or buffered sample to improve measurement accuracy. The sample can be either manually or automatically drawn. (See EG&G Princeton Applied Research, Application Note Plat-2, "Application of Polarography to the Plating Industry," 1985 for further detail.)

The diluted sample is typically analyzed using either wet chemical analysis or voltammetry. Linear sweep voltammetry is one voltammetric technique which may be used, typically in conjunction with a dropping mercury electrode. The dropping mercury electrode provides a continuously renewed interface and therefore repeatable measurement results. However, the mercury electrode is not well-suited for in-tank use due to the practical difficulties of incorporating a dropping mercury electrode into an in-tank sensor as well as the danger of inadvertent mercury contamination of the plating bath solution.

Monitoring the concentration of certain types of metal ions using currently available techniques is thus costly and time-consuming. The measurements must be performed by highly skilled personnel using specialized equipment and supplies. The techniques are not suitable for in-tank measurements. Furthermore, the delay between drawing samples and receiving measurement results can be anywhere from several hours to several days. The slow response time of the current techniques therefore limits the extent to which a high quality plating bath can be continuously maintained.

As is apparent from the above, there presently is a need for an inexpensive real time method of monitoring the concentration of metal ions within a plating bath. The method should measure metal ion content without drawing a sample of the plating bath solution or using a dropping mercury electrode. The method should complement and be easily integrated with known techniques and equipment suitable for measuring trace and major constituents, resulting in an efficient and complete plating bath analysis system.

SUMMARY OF THE INVENTION

In accordance with the present invention, a method for monitoring the concentration of metal ions within a plating bath is provided. The present invention is based upon the discovery that dc sweep voltammetry applied to a properly cleaned and activated electrode can be used to make rapid and accurate in-tank and on-line measurements of metal ion concentration. Although dc sweep voltammetry has been used for measuring diluted or buffered samples of plating bath solution using special probes, it has not heretofore been considered possible to apply these techniques to direct in-tank measurements of the solution.

The method of the present invention involves the steps of applying a pretreatment signal to a sensing electrode positioned within a plating bath solution containing metal ions. A sweep signal is then applied to the pretreated sensing electrode, producing a response signal having a voltammetric peak current which can be measured. The voltammetric peak current is proportional to the concentration of metal ions in the plating bath.

As a feature of the present invention, the method eliminates the delay, expense and complexity typically associated with presently used metal ion measurement methods. Specialized equipment and analysis personnel are no longer required. The measurement results are available on-line in real time so that desired metal ion concentration levels, and thereby the quality of the plating bath, can be continuously and efficiently maintained.

As another feature of the present invention, the response signal includes a readily identifiable current peak, the magnitude of which provides an accurate indication of metal ion concentration.

As a further feature of the present invention, the method is easily integrated with known plating bath constituent measurement methods and equipment, thus permitting measurement of all plating bath constituents using a single set of equipment. For example, in the case of an acid copper plating bath, the present invention monitors copper ions using equipment compatible with that used for monitoring trace organic addition agents, as disclosed in U.S. Pat. No. 4,631,116.

As an additional feature of the present invention, the measurements may be made using an in-tank sensor. A dropping mercury electrode is no longer required, and a variety of solid electrodes suitable for immersion in a plating bath may be used. It is therefore no longer necessary to draw a sample of the plating bath solution for analysis.

The above-discussed features and attendant advantages of the present invention will become better understood by reference to the following detailed description of the preferred embodiment and the accompanying drawings.

BRIEF DESCRIPTION OF THE DRAWINGS

FIG. 3 is a graph of the response signal voltammetric peak current as a function of copper ion concentration in acid copper plating baths.

DESCRIPTION OF THE PREFERRED EMBODIMENT

The present invention uses dc voltammetry to perform in-tank measurement of metal ion concentration levels. The method is particularly well-suited to measuring the concentration of certain types of metal ions which are typically present in high concentrations and plate at a high current efficiency, including nickel, tin and copper ions. These metal ions are typically present in a concentration of about 1 to 12 oz/gallon (7.5 to 90 grams/liter). The preferred embodiment described herein will be applied to an exemplary acid copper plating bath for purposes of demonstrating the method. It should be understood, however, that the method discloses general techniques which are useful for monitoring many other types of plating baths and the metal ions contained therein.

The exemplary system described herein is similar to the equipment used in the trace constituent analysis system disclosed in U.S. Pat. No. 4,631,116.

Figure 1:
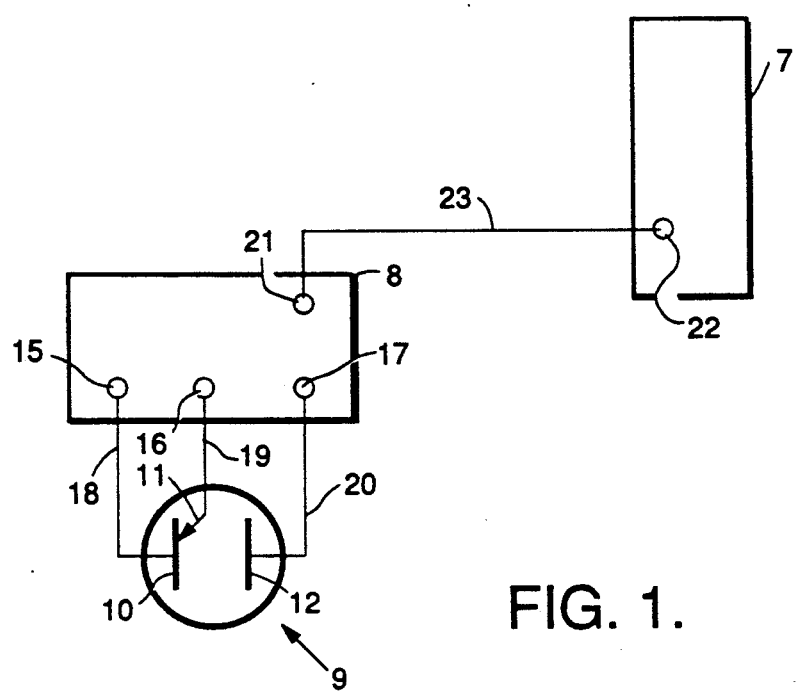
FIG. 1 is a schematic representation of a preferred embodiment for conducting the method of the present invention.

The schematic diagram of FIG. 1 illustrates a preferred embodiment of a voltammetric system used to conduct the method of the present invention. The plating bath solution is located within an electrochemical cell 9. The electrochemical cell 9 is preferably part of an in-tank electrochemical sensor submerged within the plating bath. A pump (not shown) can be used to draw the solution through the cell 9. A potentiostat 8 generates appropriate pretreatment and dc voltage sweep signals which are applied to sensing electrode 10 within cell 9 via output 15 and line 18. Alternatively, the pretreatment and sweep signals are supplied to potentiostat 8 by an external function generator (not shown). The specific characteristics of the pretreatment and sweep signals will be described in greater detail below. The potentiostat 8 limits fluctuations in the pretreatment and sweep signal waveforms resulting from changes in current flow through the electrochemical cell 9. The exemplary system of FIG. 1 uses a PAR 273 potentiostat, available from Princeton Applied Research, Princeton, N.J.

The sensing electrode 10 is preferably constructed of platinum. Other inert materials such as gold or palladium may also be used. The cell 9 also contains a counter electrode 12 and a standard calomel reference electrode 11. The reference electrode 11 and counter electrode 12 are connected to potentiostat ports 16, 17 via lines 19, 20, respectively. This three-electrode sensor design is suitable for use with many different voltammetric measurement techniques. It should be understood, however, that alternative electrode arrangements may also be used with the method of the present invention.

When the sweep signal is applied to sensing electrode 10, a response current is generated between sensing electrode 10 and counter electrode 12. Response current signal characteristics vary depending upon the electrochemical processes occurring at the surface of the sensing electrode 10. Since the electrochemical processes are a function of metal ion concentration, the response current reflects this concentration in a manner to be further discussed below.

Figure 2:
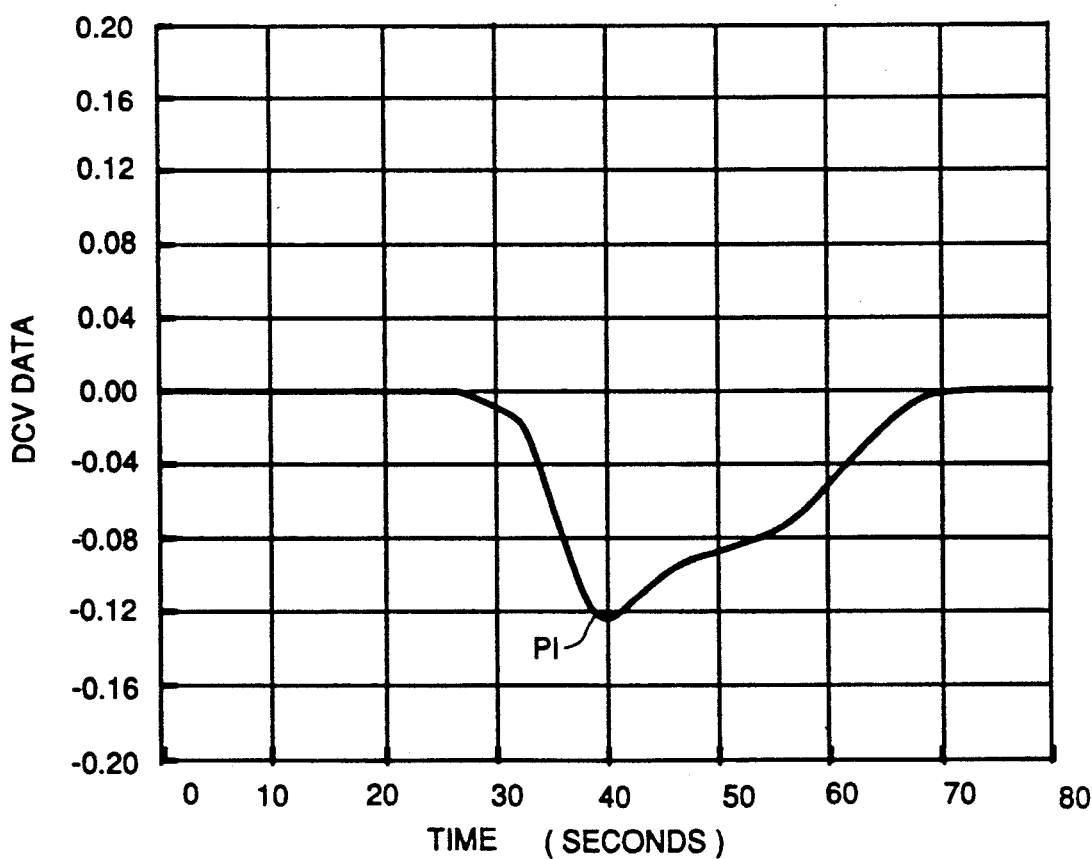
FIG. 2 shows an exemplary response signal obtained by applying the method of the present invention to an acid copper plating bath.

The response current passes back through potentiostat 8 and is applied to the input 22 of strip chart recorder 7 via line 23 from potentiostat voltage output 21. Strip chart recorder 7 displays the response current (DCV data) as a function of time as shown in FIG. 2. Alternative display or measurement means could also be used. One response current characteristic which provides an accurate indication of metal ion content is the voltammetric peak current. This peak is designated as P1 in FIG. 2. One type of voltammetric peak current is a limiting current which represents the maximum deposition current for the particular metal ion being measured. The magnitude and position of the voltammetric peak current as a function of time will therefore vary depending upon the type of metal ions present in the plating bath solution. The exemplary response current of FIG. 2 was produced by applying a dc voltage sweep to an exemplary acid copper bath containing copper ions. The response current displays thus represent unique spectra which indicate the metal ion content of the plating bath solution.

The pretreatment and sweep signal parameters used to produce response current spectra as illustrated in FIG. 2 will now be described. The pretreatment signals serve to remove organic addition agents or other plating bath constituents which may have adsorbed on sensing electrode 10. In addition, the pretreatment signal activates the electrode and prepares it for subsequent deposition of metal ions. Measurement repeatability is significantly improved by proper cleaning and activation of the electrode prior to measurement. The pretreatment signal is preferably an anodic potential of about 2 to 3 volts applied for a period of about 5 to 15 seconds. The exact potential and duration will vary depending upon the type of plating bath and the constituents it contains. In certain cases it may be preferable to apply two or more pretreatment signals in sequence prior to measurement. An example of a pretreatment signal sequence is 3 volts applied for 10 seconds followed by 1.5 volts applied for 10 seconds.

In general, the voltammetric sweep signal will be swept from about +1.0 volts to about −1.0 volts at a sweep rate of about 10 to 100 mv/second. Although the exact parameter values will vary depending upon the type of plating bath, the negative limit of the voltage sweep should be such that the metal ion maximum deposition current is reached. The response current will then exhibit a voltammetric peak current which can be used to monitor metal ion content.

The pretreatment and sweep signal parameters described above should be varied to determine the appropriate range of settings for a given plating bath. The signal parameters which should be varied include pretreatment signal potential and duration, the number of pretreatment signals applied, and the sweep signal voltage range and sweep rate. These parameters were independently varied to determine suitable ranges for using the preferred voltammetric system of FIG. 1 to monitor copper ion concentration in an exemplary LeaRonal CLX acid copper plating bath, available from LeaRonal of Freeport, N.Y. It should be emphasized that while the parameter ranges below are particularly well-suited to copper ion content measurements, the method may produce useful results using parameters outside the specified ranges.

The parameters found to be most suitable for measurement of copper ions in an acid copper plating bath are as follows. A single pretreatment signal having an anodic potential of about +3.0 volts was applied for a period of about 10 seconds. A linear dc voltage ramp signal was then applied to the sensing electrode. The ramp was swept from about +0.5 volts to about −0.6 volts at a sweep rate of about 20 mv/second. An exemplary current waveform produced in response to the sweep signal is shown in FIG. 2. The magnitude of peak P1 measures approximately 0.13 volts and corresponds to a copper ion concentration of about 2.6 oz/gallon (19.5 grams/liter).

The measurements were repeated with solutions having different copper ion concentrations to produce the calibration curve shown in FIG. 3. The curve shows the change in the magnitude of the voltammetric peak current as a function of copper ion concentration. Point P1 in FIG. 3 corresponds to the peak P1 in FIG. 2. Point P2 measures about 0.11 volts and shows the effect of reducing the copper ion concentration to about 2.2 oz/gallon (16.5 grams/liter). Point P3 measures about 0.15 volts and corresponds to an increase in copper ion content to about 2.93 oz/gallon (22 grams/liter). It can seen from FIG. 3 that the response signal voltammetric peak current is a linear function of copper ion content. Further measurements (not shown) over a range of about 1.8 to 3.6 oz/gallon (13.5 to 27 grams/liter) also conformed to the linear calibration curve of FIG. 3. In addition, the measurements are consistent with results produced using wet chemical analysis of the same solutions.

The measurements shown in FIG. 3 were performed on three distinct acid copper plating bath solutions. In addition to the differences in copper ion content, the solutions contained different concentrations of other plating bath constituents such as sulfuric acid, chloride ions and organic addition agents. Therefore, the linear curve of FIG. 3 also indicates that the method of the present invention is insensitive to the concentrations of other plating bath constituents.

Although the above description has been directed to monitoring the voltammetric peak current produced in response to a linear dc voltage sweep, this is by way of illustration and not limitation. For example, alternative voltammetric measurement signals could be used, and other signal characteristics of the response current could be monitored. It will be understood by those skilled in the art that many such alternate implementations of this method are possible without deviating from the scope of the invention, which is limited only by the appended claims.

What is claimed is:

1. A method of monitoring the concentration of metal ions within a plating bath solution, said method comprising the steps of:

applying at least one pretreatment signal to a sensing electrode positioned within said plating bath solution, producing a pretreated sensing electrode;

applying a sweep signal to said pretreated sensing electrode to thereby produce a response signal having a voltammetric peak current, said voltammetric peak current having a magnitude proportional to said concentration of metal ions; and measuring said magnitude of said voltammetric peak current.

2. The method of claim 1 wherein said metal ions constitute about 2 to 30 percent of the total weight of said plating bath solution.

3. The method of claim 1 wherein said pretreatment signal is an anodic potential of about 2 to 3 volts.

4. The method of claim 1 wherein said pretreatment signal is applied for a period of about 5 to 15 seconds.

5. The method of claim 1 wherein two pretreatment signals are applied in sequence prior to application of said sweep signal.

6. The method of claim wherein three pretreatment signals are applied in sequence prior to application of said sweep signal.

7. The method of claim 1 wherein said sweep signal is a linear dc voltage sweep signal.

8. The method of claim 7 wherein said linear dc voltage sweep signal is swept from about +1.0 volts to about −1.0 volts.

9. The method of claim 7 wherein said linear dc voltage sweep signal has a sweep rate of about 10 to 100 mv/sec.

10. The method of claim 1 wherein said plating bath is an acid copper plating bath and said metal ions are copper ions.

11. The method of claim 10 wherein said pretreatment signal is an anodic potential of about 3.0 volts.

12. The method of claim 10 wherein said pretreatment signal is applied for a period of about 10 seconds.

13. The method of claim 10 wherein said sweep signal is swept from about +0.5 volts to about −0.6 volts.

14. The method of claim 10 wherein said sweep signal has a sweep rate of about 20 mv/sec.

15. The method of claim 1 wherein said plating bath solution is contained within a plating tank and said method is performed on-line.

16. A method of monitoring the concentration of metal ions within a plating bath solution, said method comprising the steps of:

applying at least one pretreatment signal having a potential and a duration to a sensing electrode positioned within said plating bath solution, producing a pretreated sensing electrode;

applying a sweep signal having a voltage range and a sweep rate to said pretreated sensing electrode to thereby produce a response signal having a voltammetric peak current, said voltammetric peak current having a magnitude proportional to said concentration of metal ions; and measuring said magnitude of said voltammetric peak current while varying in combination each parameter comprising said potential and said duration of said pretreatment signal, and said voltage range and said sweep rate of said sweep signal, to determine the specific value of each said parameters which, when taken in combination with the remaining said parameters, provides maximum accuracy of said voltammetric peak current as an indicator of said concentration of metal ions.

* * * * *